United States Patent
Zhang et al.

(10) Patent No.: US 10,799,200 B2
(45) Date of Patent: Oct. 13, 2020

(54) PET SYSTEM WITH CRYSTAL OR DETECTOR UNIT SPACING

(71) Applicant: KONINKLIJKE PHILIPS N.V., Eindhoven (NL)

(72) Inventors: Bin Zhang, Cleveland, OH (US); Chi-Hua Tung, Aurora, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 769 days.

(21) Appl. No.: 14/909,747

(22) PCT Filed: Aug. 7, 2014

(86) PCT No.: PCT/IB2014/063764
§ 371 (c)(1),
(2) Date: Feb. 3, 2016

(87) PCT Pub. No.: WO2015/019312
PCT Pub. Date: Feb. 12, 2015

(65) Prior Publication Data
US 2016/0183893 A1 Jun. 30, 2016

Related U.S. Application Data

(60) Provisional application No. 61/862,980, filed on Aug. 7, 2013.

(51) Int. Cl.
*A61B 6/03* (2006.01)
*A61B 6/00* (2006.01)
(Continued)

(52) U.S. Cl.
CPC ............ *A61B 6/4476* (2013.01); *A61B 6/037* (2013.01); *A61B 6/0407* (2013.01);
(Continued)

(58) Field of Classification Search
CPC ... A61B 6/4476; A61B 6/0407; A61B 6/4275; A61B 6/547; A61B 6/4216; A61B 6/037;
(Continued)

(56) References Cited

U.S. PATENT DOCUMENTS

| | | | |
|---|---|---|---|
| 5,329,124 A | 7/1994 | Yamamoto et al. | |
| 6,448,559 B1 | 9/2002 | Saoudi et al. | |

(Continued)

FOREIGN PATENT DOCUMENTS

| | | |
|---|---|---|
| EP | 2138866 | 12/2009 |
| EP | 2273285 | 1/2011 |

(Continued)

*Primary Examiner* — David P Porta
*Assistant Examiner* — Shun Lee

(57) ABSTRACT

A nuclear scanner includes an annular support structure (12) which supports a plurality of radiation detector units (14), each detector unit including crystals (52), tiles (66) containing an array of crystals, or modules (14) of tiles. The detector units define annular ranks of crystals, and the annular ranks of crystals define spaces between the ranks. In another embodiment, the crystals define axial spaces between crystals. Separate rings of crystals have axial spaces that are staggered such that no area of the imaging region is missed. The spaces between the detector units may be adjusted to form uniform or non-uniform spacing. Moving the patient through the annular support structure compensates for reduced sampling under the spaces between ranks.

19 Claims, 8 Drawing Sheets

(51) Int. Cl.
*A61B 6/04* (2006.01)
*G01T 1/29* (2006.01)

(52) U.S. Cl.
CPC .......... *A61B 6/0457* (2013.01); *A61B 6/4216* (2013.01); *A61B 6/4258* (2013.01); *A61B 6/4266* (2013.01); *A61B 6/4275* (2013.01); *A61B 6/54* (2013.01); *A61B 6/547* (2013.01); *G01T 1/2985* (2013.01)

(58) Field of Classification Search
CPC ... A61B 6/0457; A61B 6/4258; A61B 6/4266; A61B 6/54; G01T 1/2985
See application file for complete search history.

(56) References Cited

U.S. PATENT DOCUMENTS

| | | |
|---|---|---|
| 7,099,429 B2 | 8/2006 | Hoffman et al. |
| 7,132,664 B1 | 11/2006 | Crosetto et al. |
| 8,415,631 B2 | 4/2013 | Moriyasu |
| 2003/0161521 A1 | 8/2003 | Newport et al. |
| 2010/0128956 A1* | 5/2010 | Yamaya ................ G01T 1/1611 382/132 |
| 2010/0294940 A1* | 11/2010 | Wieczorek ............ G01T 1/2018 250/363.03 |
| 2011/0031407 A1* | 2/2011 | Yamaya ................ G01T 1/2985 250/363.03 |
| 2011/0297840 A1 | 12/2011 | Tanaka et al. |
| 2012/0104263 A1 | 5/2012 | Gagnon |

FOREIGN PATENT DOCUMENTS

| | | |
|---|---|---|
| WO | 2010/109586 | 9/2010 |
| WO | 2013/074894 | 5/2013 |

\* cited by examiner

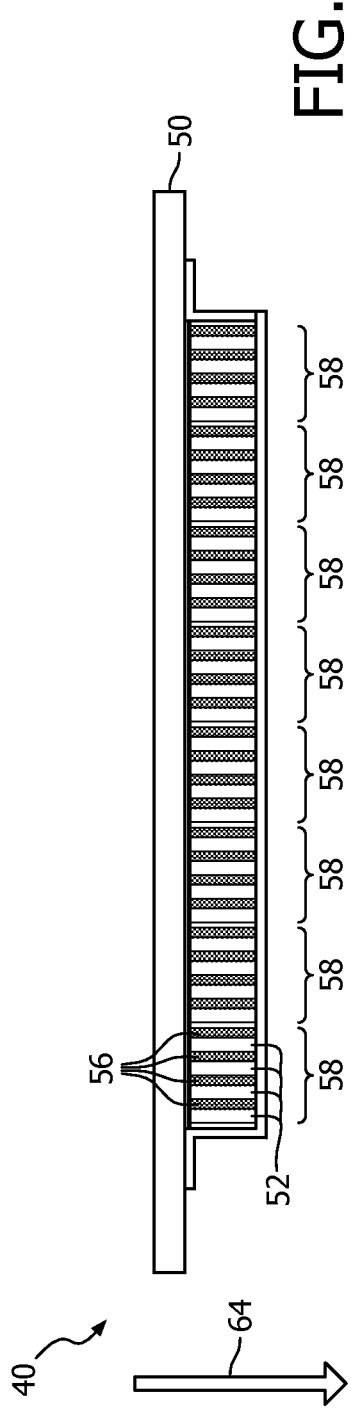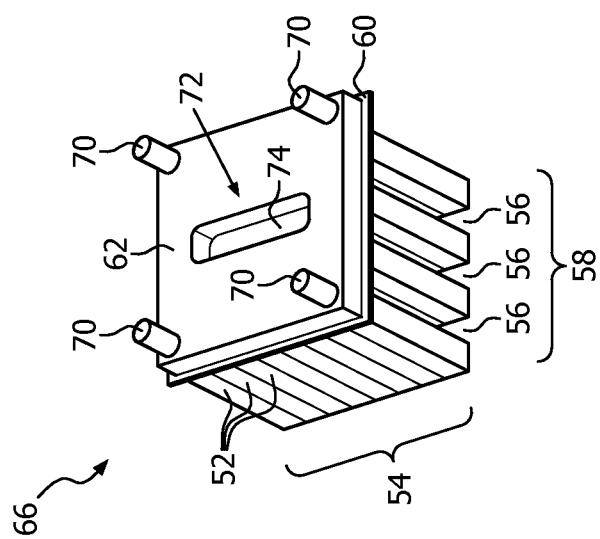

PET SYSTEM WITH CRYSTAL OR DETECTOR UNIT SPACING

CROSS REFERENCE TO RELATED APPLICATIONS

This application is the U.S. National Phase application under 35 U.S.C. § 371 of International Application No. PCT/IB2014/063764, filed Aug. 7, 2014, published as WO 2015/019312 on Feb. 12, 2015, which claims the benefit of U.S. Provisional Patent Application No. 61/862,980 filed Aug. 7, 2013. These applications are hereby incorporated by reference herein.

The present application relates to diagnostic imaging systems and methods. It finds particular application to positron emission tomography (PET), but may find application in other imaging systems.

In a PET scan, a patient receives a dose of a radiopharmaceutical. The pharmaceutical is carried through the blood and concentrates in one or more target organs or regions and emits radiation. During a nuclear scanning procedure, the emitted radiation is detected by the system and reconstructed into an image of the distribution of the radiopharmaceutical in the patient. The image can show the circulatory system and/or the relative absorption of the radiopharmaceutical in various regions or organs. Cancerous tumors, for example, absorb significant quantities of glucose containing radiopharmaceuticals. Integration of anatomical data from an anatomical scanning procedure with the metabolic data from the nuclear scanning procedure in a hybrid image gives physicians visual information to determine the radioisotope distribution in the anatomy of the subject.

Solid-state PET detectors are usually made of scintillator crystals formed into 2D block arrays coupled to an array of detector diodes. The array is coupled to a Printed Circuit Board (PCB) to form a detector tile (sometimes called a stack). The tile is then plugged into a bigger PCB (a module) which holds multiple tiles. The detector tiles are often mounted in a configuration having more than 2×2 tiles (e.g., 4×5, 4×6, or 4×7). The crystals in the 2D block arrays typically abut each other and, in general, there is no or negligible spacing between crystals and modules. Crystal cost is currently a large portion of the hardware cost. The size of the Field of View (FOV) that a PET system can cover is directly determined by the number of crystals used which makes large FOV systems costly.

The present application proposes to address these problems by reducing the number of crystal without reducing the FOV or, alternatively, enlarging the FOV without adding crystals, all while maintaining uniform sampling without reducing resolution.

A PET scanner is disclosed which includes an annular support structure which surrounds an examination region extending axially parallel to an axis of the annular support structure. The PET scanner further includes a plurality of radiation detector units mounted on the annular support structure, forming annular ranks surrounding the examination region, and a patient support which moves a patient axially in the examination region, wherein at least some of the annular ranks are spaced by annular gaps.

A generally annular PET device is also disclosed which includes a first annular ring supporting at least a first ring of scintillation crystals, a second annular support ring supporting at least a second ring of scintillation crystals and being moveable with respect to the first annular support ring to change the spacing between the first and second rings of crystals, and a patient support which moves a patient in the PET device during a scan.

A method of performing a PET scan is also disclosed which includes the steps of positioning a patient on a patient support of a PET scanner, moving the patient with the patient support through a plurality of rings of radiation detector units which are spaced by at least one annular gap to collect PET data, and reconstructing the PET data to produce a patient image.

One advantage resides in decreased cost.

Another advantage lies in increased FOV.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

FIG. 1 diagrammatically illustrates a positron emission tomography (PET) scanner having adjustable spacing between rings.

FIG. 2 illustrates an individual PET detector module with the scintillation crystals in a spaced configuration.

FIG. 3 illustrates a tile with its attached photodetector and scintillation crystals in a spaced configuration.

Figure 10:
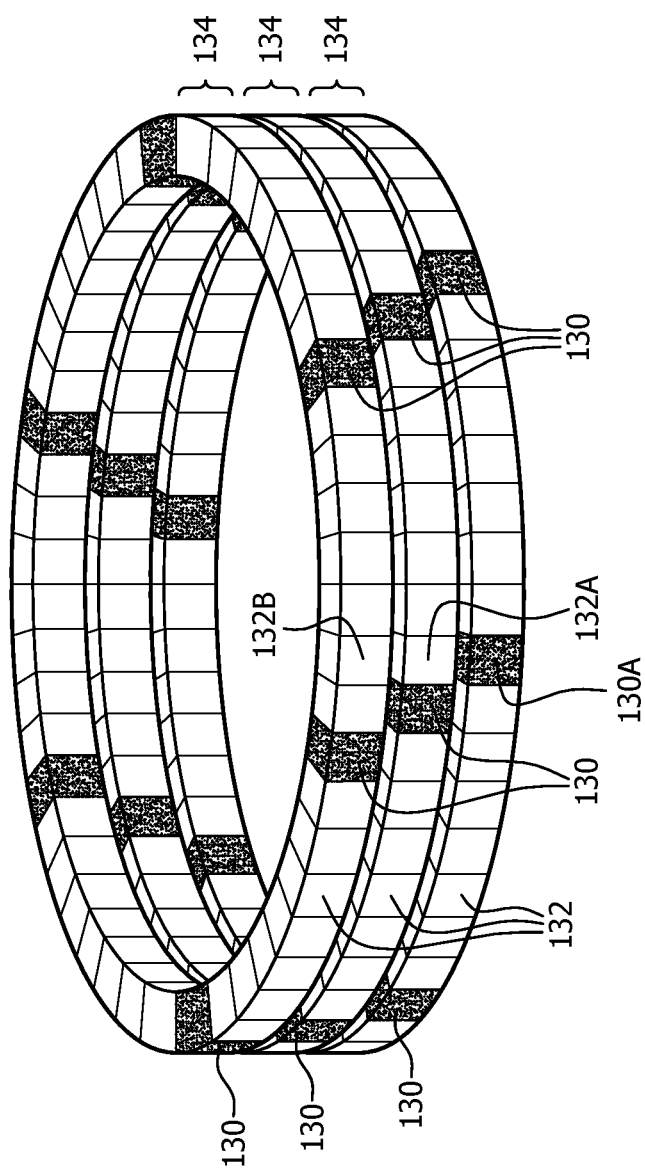

FIG. 10 diagrammatically illustrates a spaced arrangement of detector units on a PET detector ring in one embodiment.

Figure 11:
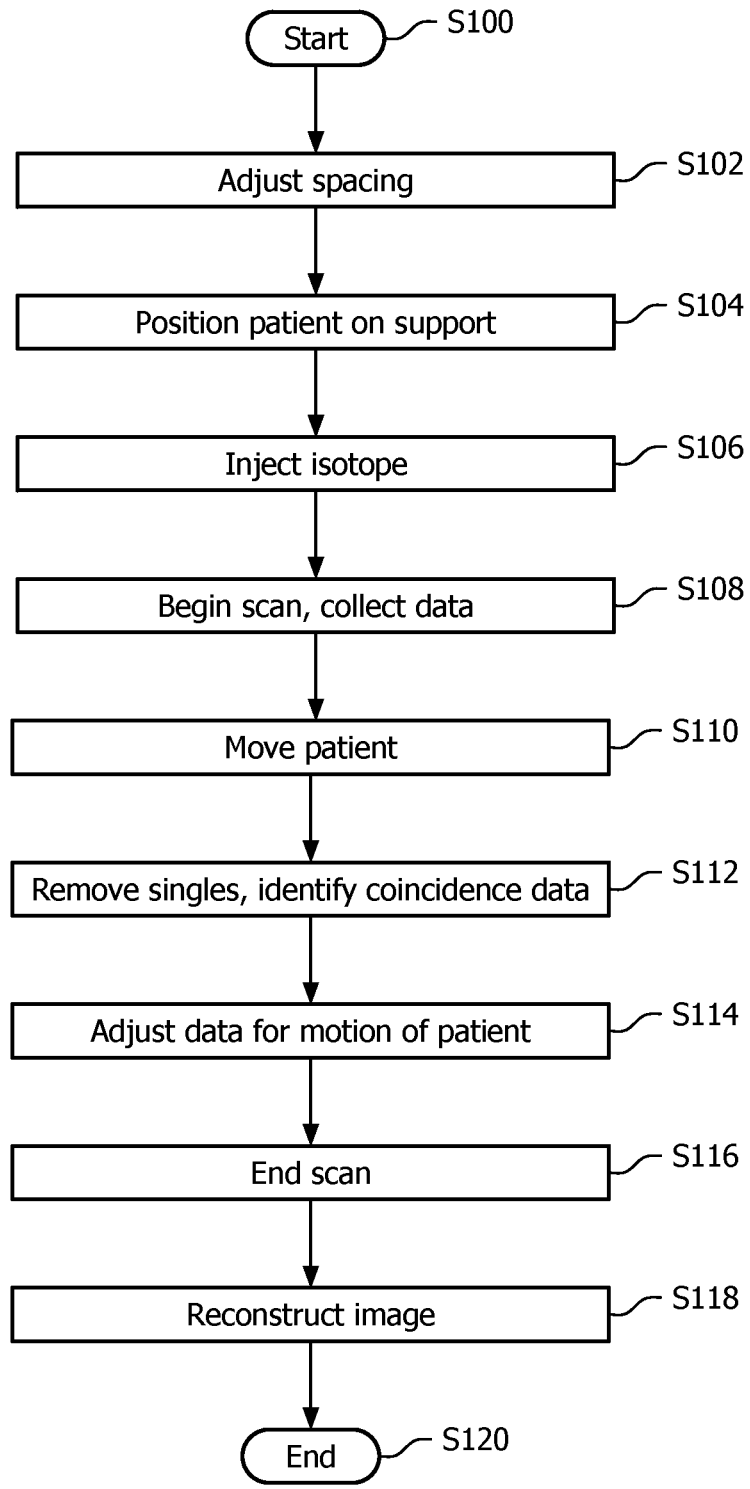

FIG. 11 is a flow chart illustrating a method for scanning a patient with a PET scanner having sparse detector units.

Figure 12:
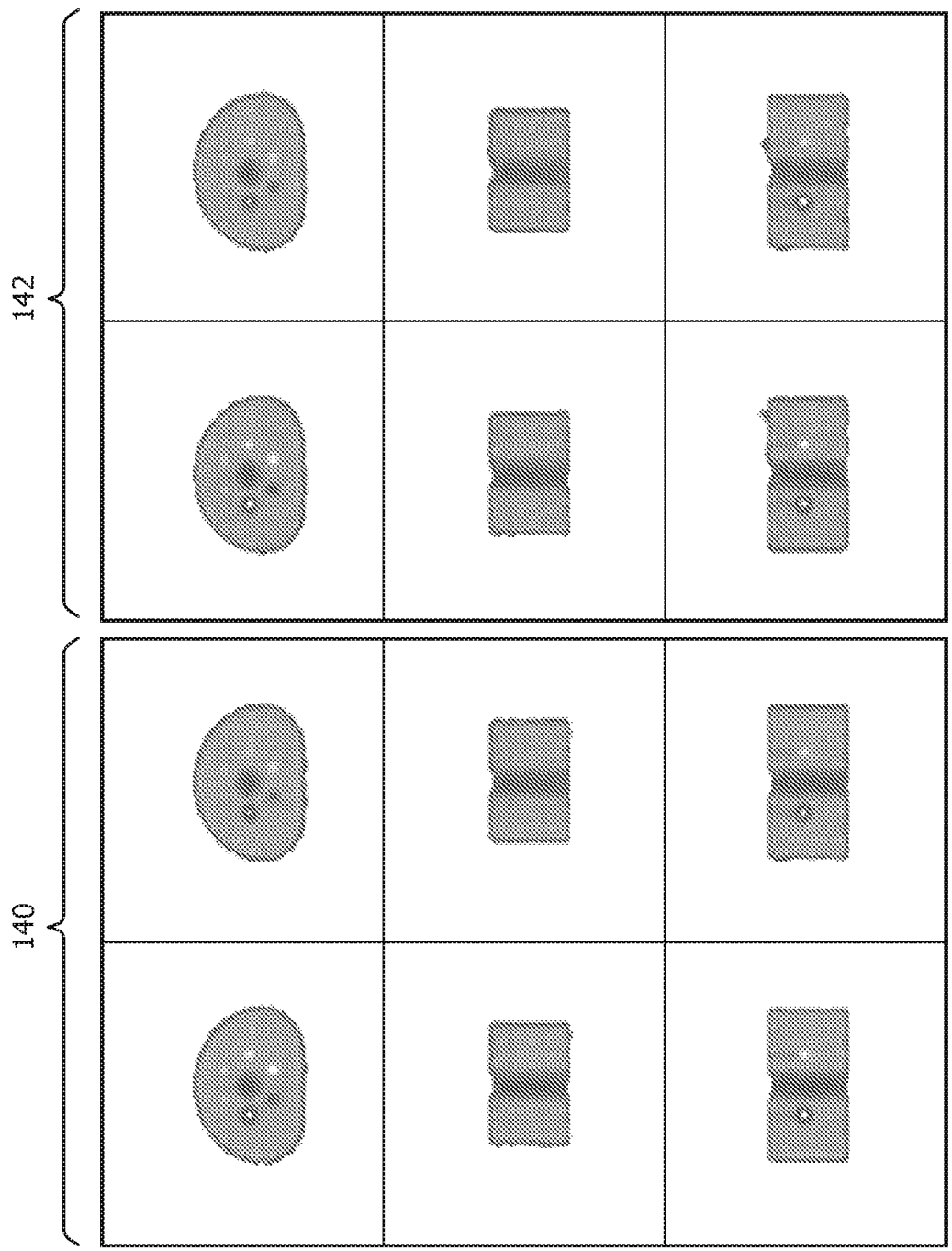

FIG. 12 illustrates several PET scans with data from every fourth rank of crystals removed to illustrate that removing crystals does not sacrifice scan quality.

Figure 1:
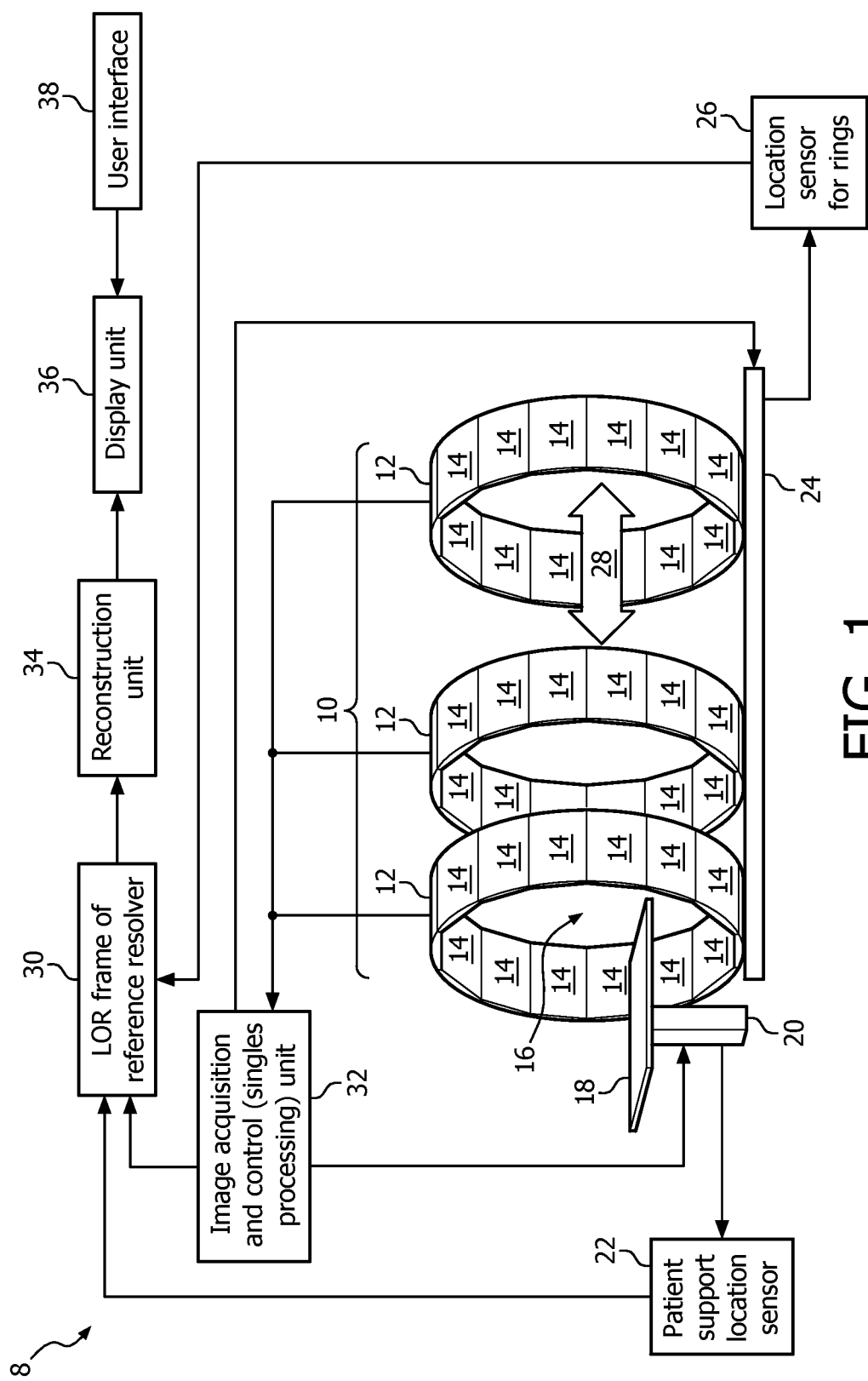

With reference to FIG. 1, an imaging system 8 includes a positron emission tomography (PET) imaging system 10 and, optionally, includes an anatomical imaging system, such as a CT scanner (not shown). The PET scanner 10 includes a plurality of rings 12 of detector units 14 housed within a gantry (not shown). The rings define a patient receiving bore 16. The imaging system 8 further includes a patient support 18, a patient support drive unit 20, and a position sensor 22 for the patient support unit. The rings 12 are moveable by a ring positioner 24 (e.g., a motorized track, worm gear, etc.). A ring location sensor 26 outputs the locations and rotational positions of the rings 12 to a line-of-response (LOR) and frame of reference resolver 30.

In PET scanning, a suitable positron-emitting radiopharmaceutical is administered to the subject prior to the PET data acquisition. The emitted positrons undergo positron/electron annihilation, each annihilation event generating 511 keV gamma rays travelling in opposite directions, thus defining a line of response (LOR). The patient support 18 positions the patient or subject to be imaged into the examination region 16. An image acquisition and control unit 32 operates the patient support drive unit 20, the ring positioner 24, and the PET rings 12 to acquire the PET line-of-response data (optionally including time-of-flight localization). The image acquisition and control unit 32 monitors each detector unit 14 for an energy spike, e.g., integrated area under the pulse, characteristic of the energy of the gamma rays generated by the radiopharmaceutical. The image acquisition and control unit 32 checks a clock and time stamps each detected gamma ray event with a time of leading edge receipt. When the gamma rays strike the detectors, the location on the struck detector unit, the location of the detector unit in the ring, the location of the moveable ring, and the strike time are recorded. These locations, with the location of the patient support, provide an indication of each gamma ray strike in the coordinate system of the patient. The Image Acquisition and Control Unit 32 includes a singles processing unit that monitors the recorded gamma ray events for single gamma ray events that are not paired with a temporally close event, rejecting the single events.

Once an event pair is verified by the image acquisition and control unit 32, the LOR is defined and stored as PET line-of-response data in a list mode event storage memory. The PET line-of-response data also includes the time stamps and end point crystal locations. The PET line-of-response data is communicated to the LOR frame of reference resolver 30, which combines the line-of-response data with the patient support position and rings to place the line-or-response data in a frame of reference which moves with the patient such that, in the frame of reference, the patient is stationary. The LOR frame of reference resolver 30 resolves the line-of-response data into the frame of reference to produce resolved line-of-response data, which is communicated to the reconstruction unit 34. The PET reconstruction processor 34 uses an image reconstruction algorithm to generate one or more PET images. An attenuation map, e.g., from a CT scanner, is used by the PET image reconstruction processor to generate an attenuation corrected PET image representation from the PET data. Advantageously, an iterative reconstruction algorithm such as Maximum-Likelihood Expectation Maximization (ML-EM) and Ordered subset expectation maximization (OS-EM) may be used.

The data may be stored in a list-mode or may be processed as sinogram data. The PET line-of-response data is combined with the CT image to provide functional and anatomical information.

The imaging acquisition and control unit 32, LOR frame of reference resolver 30, and reconstruction unit 34 are suitably embodied by one or more digital processors or controllers, or by a combination of digital processors or controllers, operating in combination with suitable electronics, power supplies, and so forth. The reconstruction unit 34 optionally includes dedicated reconstruction pipeline hardware embodied, for example, as application-specific integrated circuitry (ASIC) hardware. The reconstruction unit 34 combines the resolved line-of-response data and stores the resulting images in an image memory for display on a display unit 36 (e.g. a computer including a monitor). A user interface 38 interfaces with the display unit 36, the image acquisition and control unit 32, the reconstruction unit 34, the ring positioner 24, the image memory, and the like to enable a radiologist or other user to configure, initiate, and monitor the PET imaging sessions and to enable the radiologist or other user to view the resulting PET images. The display unit 36 includes a display, such as an LCD display. The user interface 38 may include one or several input devices such as a keyboard, mouse, touch-sensitive screen, or so forth.

The detector units 14 may be formed of individual scintillation crystals, an array of scintillation crystals, a tile, or a module. Spacing the modules is mechanically the least challenging.

FIG. 2 illustrates a detector module 40 which includes a cooling and support plate assembly 50 with scintillation crystal arrays 58 mounted underneath the assembly 50. In one embodiment, a plurality of scintillator crystals 52 are arranged in ranks 54 (see FIG. 3) which alternate with spaces 56 to form the crystal arrays 58, which are optically coupled to a plurality of photo detector arrays 60 (see FIG. 3). The detector array is mounted to a tile mount 62 (see FIG. 3) which mounted to the cooling plate 50. The space 56 is a crystal-width wide between crystal ranks 54 which are also a single crystal-width wide, providing the same field of view (FOV) with fewer crystals. In the embodiment of FIG. 2, the module 40 would be combined other identical modules on a ring 12. In another embodiment, the scintillator crystals 52 are closely packed.

The detector modules 40 have a predetermined crystal spacing 56 to reduce the overall system cost with negligible image quality loss by providing the same field of view (FOV) with fewer crystals. In another embodiment, discussed below, the tiles or modules are spaced. Spacing the crystals, tiles, or modules enables a longer PET axial FOV with a similar number of crystals as compared to a PET scanner with a conventional crystal layout or, alternatively, enables a low-cost PET scanner without significant sacrifice of image quality by reducing the number of crystals. Currently, silicon photo multipliers (Si-PMs) are replacing photomultipliers in PET detector design, and Si-PMs are also an expensive resource. The number of Si-PMs is directly proportional to the number of crystals, so reducing crystals also reduces the number of Si-PMs.

In the orientation of FIG. 2, down, indicated by arrow 64, is toward the center of the scanner examination region 16. Elements arranged along the circumference of the annular rings 12 will be referred to as being arranged annularly. For example, referring to FIG. 1, the detector units 14 are arranged annularly. In the embodiment of FIG. 2 in which each detector unit 14 is a detector module 40, the crystal ranks 54 form annular rings of crystals 52. Elements arranged parallel to axis 28 passing through the center of the examination region 16 are referred to as axial.

The width of space 56 may be either fixed or adjustable by, for example, omitting tiles, using a different cooling and support plate 50, or using tracks or different holes in the cooling support plate 50. The module 40 may have different mount points or tracks to allow movement on the rings. The rings 12 are also movable.

With reference to FIG. 3, a tile 66 is shown. The tile 66 includes a scintillation crystal array 58 optically connected to photodetectors 60 which are attached to the tile mount 62. Pins 70 mechanically position the tile mount 62. The tile mount 62 has an aperture 72 through the top surface for a connector 74. The array 58 has crystals 52 arranged in ranks 54, with a space 56 one crystal wide separating the ranks 54. The pattern of spaces and crystals would be continued on other tiles of the same module, and then on tiles of other modules, so that the ranks form rings (attached to annular rings 12) around examination region 16.

Figure 4:
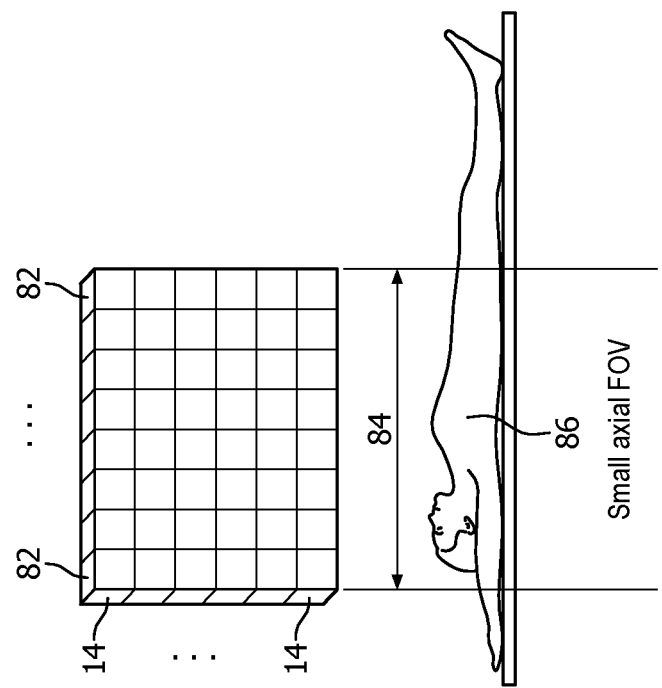
FIG. 4 illustrates a prior art abutting arrangement of rings of detector units.

FIG. 4 shows a prior art arrangement of detector units 14 in ranks 82 with no spacing between crystals, modules, and rings. Based on data sufficiency theories, the lines of response (LORs) generated by the detector units 14 of FIG. 4 are over-sampled, e.g., redundant, for an exact image reconstruction.

Iterative image reconstruction algorithms (e,g, ML-EM and OS-EM) used by PET systems are less sensitive to lower sampling of 3D measurements compared to legacy analytical algorithms, so a PET system with predetermined detector unit spacing (e.g., crystal, tile, and/or module spacing) can make better use of the crystals and Si-PM components with reduced data redundancy in the 3D PET measurement, essentially providing the same resolution with reduced cost.

Figure 5:
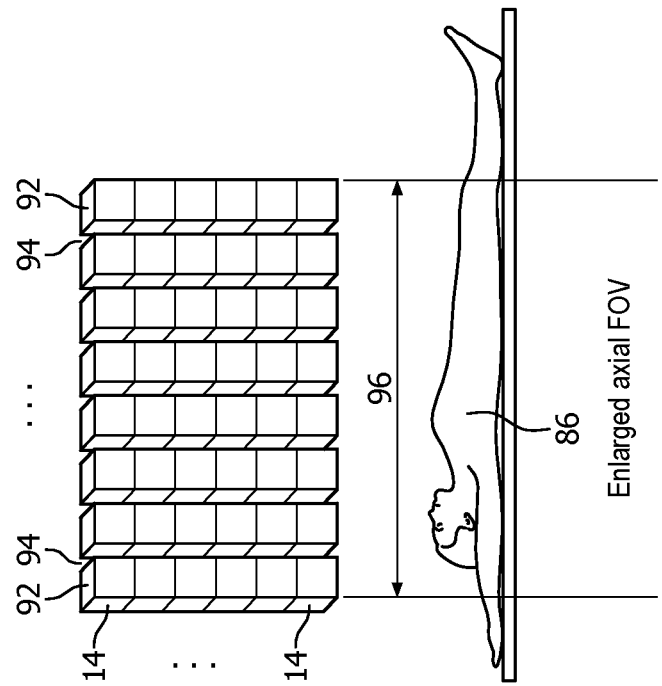
FIG. 5 illustrates a spread arrangement of rings of detector units having uniform spacing.

The spacing of the detector units 14 can be designed as either uniform or variable based on factors such as the cost of the system, image quality requirement, FOV 84, the sensitivity profile of the scanner coverage, the design needs for a crystal/ring based cost efficient system, etc. FIG. 5 shows a uniform, spread arrangement of detector units 14 in spaced ranks 92 having annular spaces 94 there between. In one embodiment, the spaces are slightly narrower than the width of one detector unit 14. This arrangement provides an enlarged FOV 96 in the axial direction (parallel to the axis of the patient receiving bore 16), allowing the scanner to cover patient 86 more quickly. The ranks 92 form a portion of the annular ring 12 of crystals 90 surrounding examination region 16.

Figure 6:
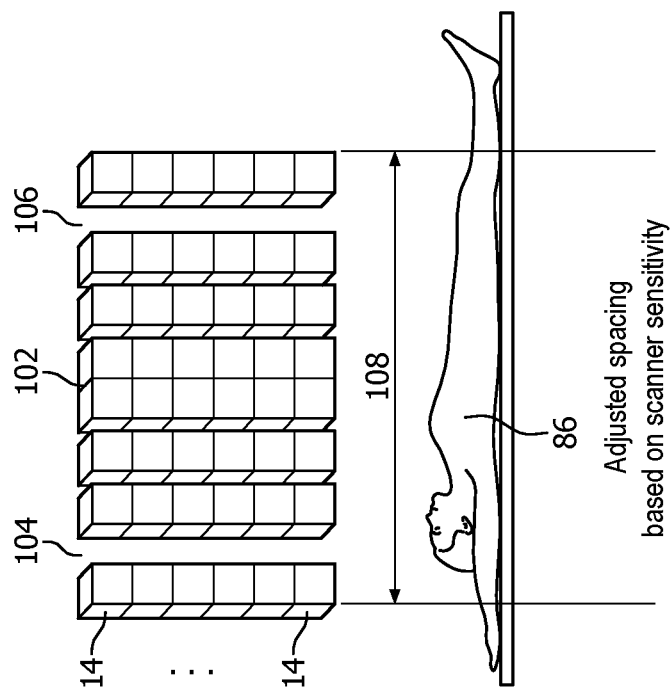
FIG. 6 illustrates a spread arrangement of rings of detector units having increased sensitivity in the center of the imaging region.

In some embodiments, the spaces 94 between the ranks 92 may contain shields (e.g., an annular ring of shielding) to prevent photons from entering the side crystals of the units from the side rather than the radiation detection face. In embodiments in which the interactions due to photons entering the side of the crystal can be distinguished from interactions caused by a photon hitting the face of the crystal, shielding is unnecessary and may block useful data. Interactions produced by photons entering the side of the crystal may be used to estimate events that would have been detected by a detector ring disposed in the gap. The spacing need not be uniform. Variable detector unit spacing is also contemplated. FIG. 6 shows an arrangement having the detector units 14 spaced by non-constant width annular spaces, the spacing varying from the center at 102 where there is minimal spacing to larger spaces 104, 106 adjacent the ends of the FOV 108. This scheme is used when high resolution is wanted in a small examination area, and reduced resolution in the surrounding areas is acceptable.

The spacing may be accomplished by spacing the individual crystals 52, by spacing the detector units 14, or by spacing the rings 12 to which the detector units 14 are affixed, or any combination thereof. In the embodiment of FIG. 1, the rings are movable to accommodate a user selected configuration. In an embodiment with multiple ranks of detector units 14 on a ring, there may be space between units. For example, it is contemplated that the pattern of FIG. 6 could continue across tiles 66, with central tiles having closer spacing and tiles that are at the ends of the module having wider spacing. In one embodiment, the individual crystals have fixed spacing on the tile (either variable or uniform), but the position of the tiles on the module can be adjusted by using different holes (or sliding on tracks) or by omitting tiles. The modules 40 themselves may also be adjustable on the axial ring.

Figure 7:
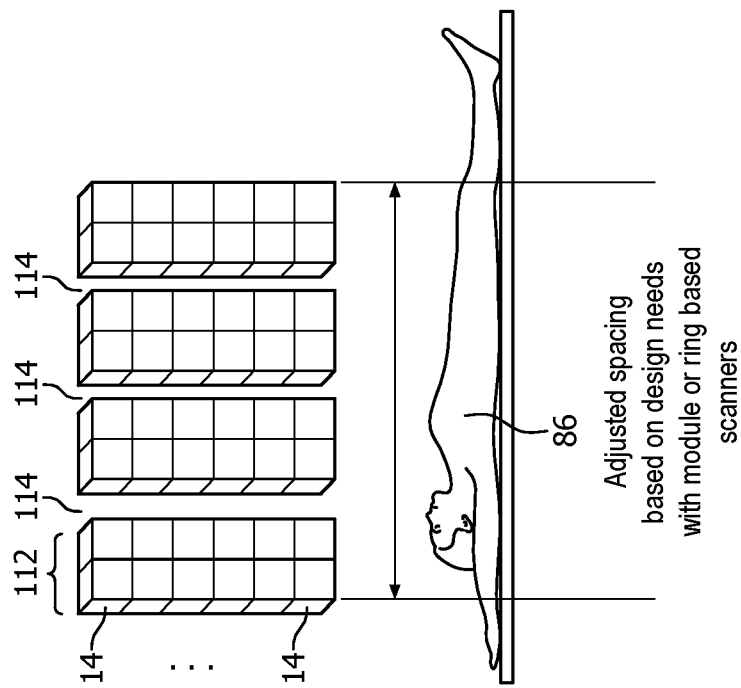
FIG. 7 illustrates an arrangement in which pairs of rings of detector units are spaced uniformly.

FIG. 7 shows an arrangement in which the detector rings 12 are arranged in pairs 112 of ranks of detector modules 14 with annular spaces 114 between pairs of ranks. The pairs 112 of detector modules 14 may be tiles which are two crystals wide with spaces between tiles. The tiles may be wider in other embodiments, e.g., eight crystal widths wide.

In another embodiment, the detector units 14 may be modules containing closely packed tiles, and the modules may have space between them. In another embodiment, the crystals may be mounted in pairs (or larger numbers) of ranks mounted on movable rings (e.g. 8 ranks of crystals mounted on five rings).

Figure 8:
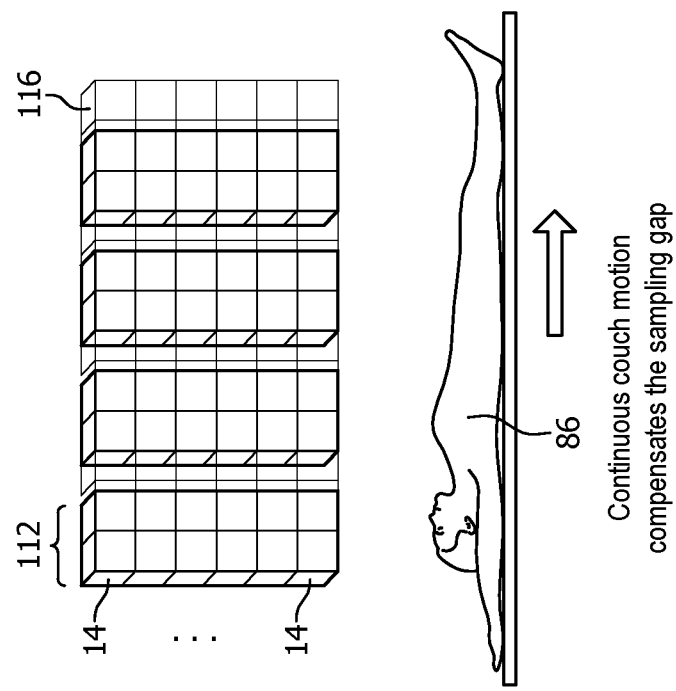
FIG. 8 illustrates patient support movement with respect to rings of detector units.

In embodiment such as FIG. 5-7, the gaps may be large enough to create rings of reduced sensitivity to regions directly under the each annular space, creating artifacts in the reconstructed patient image. Moving the patient support in the PET imaging system compensates for the reduced number of samplings under the annular spaces to create uniform sampling. In such an embodiment, the patient support moves the patient to ensure that all regions of the patient are uniformly sampled. As the patient is moved, different portions of the tile array image the patient, shown by the ghosted crystals 116 in FIG. 8. The patient may be moved continuously or, alternatively, step-wise, from one position to another, pausing briefly at certain positions. The patient can be moved through the bore or may move back and forth, e.g., over a distance equal or greater than a gap plus a detector ring.

Figure 9:
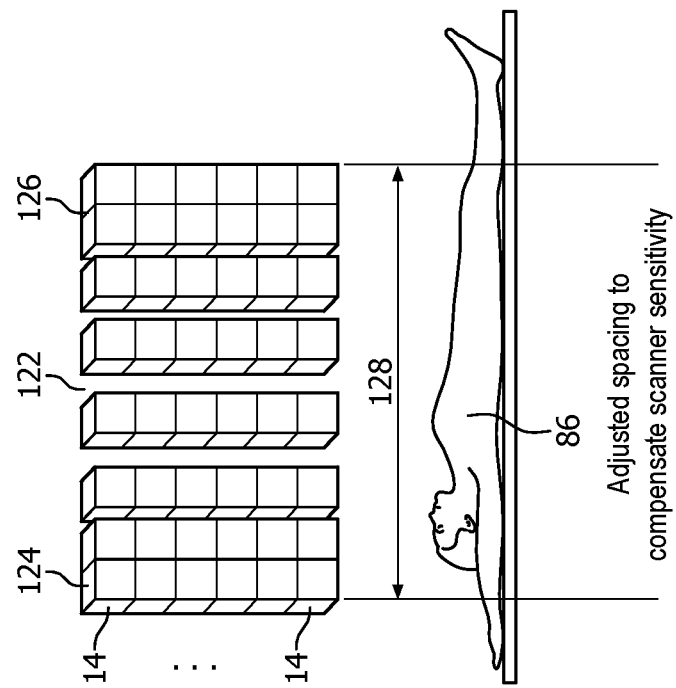
FIG. 9 illustrates an arrangement of rings of detector units in which the spacing compensates for reduced scanner sensitivity adjacent to axial ends of the FOV.

The detector units 14 may be arranged to compensate for scanner sensitivity. The scanner has greater sensitivity in the center of the array because an emission event in the center has a greater probability of striking a crystal than an emission event on the edge of the array. FIG. 9 shows an arrangement to compensate for this and provide uniform scanner sensitivity. The detector units 14 near the center of the imaging region may have a wider gap 122 than the units at the edges 124, 126 of the array. This provides for greater data collection at the edges of the FOV 128 which are typically less densely sampled.

FIG. 10 shows an embodiment in which gaps 130 within each ring 134 are staggered from one ring to the adjacent ring such that, when the patient is moved on the patient support parallel to the axis of the bore, the gaps 130 are imaged by detector units 132 of other rings. In FIGS. 5-9, the spaces between detector units separated annular ranks of detector units. FIG. 10 has spaces between rings 134 of detector units 132 but also includes annular gaps 130 within the annular ring. It is to be understood that annular gaps 130 are larger gaps, e.g., on the order of size of a crystal or tile. There may be smaller openings due to mechanical tolerances or mounting construction which have no effect on image resolution and are ignored for purposes of FIG. 10. In the embodiment of FIG. 10, the gaps are regular, that is, each pair of gaps defines the same length of arc of the circumference. No portion of the gaps 130 of one ring 134 aligns with a gap of an adjacent ring. In an embodiment with more rings, the gaps of non-adjacent rings may overlap. Because the gaps 130 are staggered, all areas of the patient are imaged, e.g., gap 130A is imaged by detector units 132A and 132B as the patient is moved. The circumferential gaps 130 may be between tiles in the PET crystal rings 134. In another embodiment, there may be gaps between modules on the PET detector rings. The gaps 130 may including shielding. The position of rings 134 may be adjustable to alter the space between rings. The rings 134 may be rotated, particularly if the position or size of the gaps 130 is altered.

FIG. 11 shows an exemplary method for use with the embodiments.

The method begins at S100.

At S102, the spacing between the detector units (e.g. crystals, tiles, or modules) is adjusted. In one embodiment, the position of the crystals is known mechanically by the location of the mounts for the crystals, tiles, or modules.

Alternatively or additionally, the position of the crystals may be calculated by a point source introduced into the bore of the PET scanner.

At S104, the patient is positioned on the patient support (e.g., couch).

At S106, the radionuclide (isotope) is injected.

At S108, the scan begins and PET data is collected e.g., in a list mode. The PET data includes patient position, time of gamma ray detection, and detecting crystal location.

At S110, the patient is moved in the imaging region and the locations of the detecting crystals are transformed into the coordinate system of the patient or another coordinate system that adjusts for patient motion.

At S112, coincidence of pairs of positron emission events are detected, single events which are not part of a pair are removed, and, optionally, Time Of Flight (TOF) is calculated for each coincident pair of events.

At S114, the data is adjusted to place the data in a frame of reference which is stationary with respect to the patient.

At S116, the scan ends.

At S118, the image is reconstructed. Optionally, reconstruction starts during the scan. The reconstructed 3D image uses the geometry and crystal location information and an iterative reconstruction algorithm that is not sensitive to the discontinuous samplings. The continuous table motion fills in any missing sampling data caused by spaces between crystals.

At S120, the method ends.

Crystal spacing can be designed to reduce the cost of a PET system significantly to build cost-efficient PET systems without significant loss of image quality. FIG. 12 shows a comparison study between a current clinical reconstruction and a reconstruction with clipped data that simulates the impact of a crystal separation of 1 ring for every 4 rings. The image was generated from a test phantom which simulates a human torso. As shown by a visual comparison of the left images 140 which were produced using a current time of flight PET reconstruction with the right images 142 which were produced with 9 rings of data removed (rings 2, 7, 12, 17, 22, 27, 32, 37, and 42 of the 44 rings). From this comparison, it can be seen that a reduction of about 20% of the crystals results in minimal image degradation. In this case, the spacing is one crystal width wide separating ranks of crystals four crystal wide. In another embodiment, the spacing could be uniform, with a space roughly a quarter crystal wide between each rank of crystals, the ranks being only one crystal wide.

The spacing should not be so great that artificial crystals must be created by interpolation to fill in the spaces during reconstruction.

The disclosed PET system allows spacing between adjacent crystals, tiles, detector modules, or detector rings. The spacing can be either uniform or non-uniform and may be adjustable or fixed, depending on imaging application needs. The exact geometric location of each crystal can be exported or calculated based on the spacing. Continuous or step-wise table movement may be utilized to compensate the discontinuous sampling due to crystal or module spacing. The acquired 3D data may be either sinogram or list-mode data. The reconstructed 3D image uses the geometry and crystal location information and an iterative reconstruction algorithm that can handle the discontinuous samplings or continuous table motion.

Other types of detectors are contemplated besides a Silicon Photomultiplier (SiPM) detector coupled with a scintillation crystal. A Cadmium Zinc Telluride (CZT) or other solid state detector is contemplated. A scintillation crystal array coupled with a photomultiplier tube is also contemplated. The detector or the crystal may be pixilated. Anger logic may be used. The system may be used in a hybrid scanning system which is a PET/CT or a PET/MR system.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A PET scanner comprising:
   an annular support structure which surrounds an examination region, the examination region extending axially parallel to an axis of the annular support structure;
   a plurality of radiation detector units mounted on the annular support structure, each radiation detector unit comprising a plurality of scintillator crystals, and wherein the scintillator crystals of the plurality of radiation detector units are arranged in annular ranks that surround the examination region; and
   wherein at least some of the annular ranks are spaced by annular gaps within each of the plurality of radiation detector units.

2. The PET scanner according to claim 1, further including a mechanism which adjusts the annular gaps.

3. The PET scanner according to claim 1, wherein the gaps are smaller adjacent a center of the examination region and progressively larger toward axially opposite ends of the examination region.

4. The PET scanner according to claim 1, wherein the gaps are larger adjacent a center of the examination region and progressively smaller toward axially opposite ends of the examination region.

5. The PET scanner according to claim 1, wherein the annular gaps are uniform in axial length.

6. The PET scanner according to claim 1, further comprising a patient support that is configured to move a patient axially in the examination region, wherein the patient support is configured to move the patient in the examination region during the scan.

7. The PET scanner according to claim 6, further including a sensor configured to determine a location of the patient support and a location unit configured to determine a location of the annular support structure.

8. The PET scanner according to claim 7, wherein line of response data from the annular support structure is translated from a frame of reference of the location of the annular support structure to a frame of reference which moves with the patient support.

9. The PET scanner according to claim 1, wherein shields are disposed in the annular gaps.

10. The PET scanner according to claim 1, wherein the gaps are ¼ of an axial length of one of the detector units.

11. The PET scanner according to claim 1, wherein the radiation detector units of the plurality of radiation detector units are arranged in radiation detector unit annular ranks including:
    a first radiation detector unit annular rank which includes a first plurality of circumferential gaps between the plurality of radiation detector units which form the first radiation detector unit annular rank; and
    a second radiation detector unit annular rank which includes a second plurality of circumferential gaps between the plurality of radiation detector units which form the second radiation detector unit annular rank, the first plurality of circumferential gaps being staggered with respect to the second plurality of circumferential gaps such that no portion of the first plurality of circumferential gaps aligns axially with the second plurality of circumferential gaps.

12. The PET scanner according to claim 1, wherein the plurality of radiation detector units include radiation detector units at a center of the examination region.

13. A method of performing a PET scan comprising:
collecting PET data by moving a patient with a patient support through a plurality of rings of radiation detector units, each radiation detector unit comprising a plurality of scintillator crystals, and wherein the scintillator crystals of the plurality of radiation detector units are arranged in annular ranks that surround an examination region, and at least some of the annular ranks are spaced by annular gaps within each of the plurality of radiation detector units; and reconstructing the PET data to produce a patient image.

14. The method according to claim 13, wherein the patient support is moved one of continuously or step-wise.

15. The method according to claim 14, further including: adjusting the annular gap.

16. The method according to claim 13, further including:
detecting the location of the patient support; and
detecting the location of the plurality of rings of radiation detectors.

17. The method according to claim 13, further including:
translating line of response data from a frame of reference of the plurality of rings to a frame of reference which moves with the patient support.

18. The method according to claim 13, wherein the annular gaps are smaller adjacent a center of the examination region and progressively larger toward axially opposite ends of the examination region.

19. The method according to claim 13, wherein the annular gaps are larger adjacent a center of the examination region and progressively smaller toward axially opposite ends of the examination region.

* * * * *